United States Patent [19]

Agdanowski et al.

[11] 4,346,711

[45] Aug. 31, 1982

[54] BODY FLUID COLLECTION DEVICE WITH DISPOSABLE LINER

[75] Inventors: Ronald T. Agdanowski, St. Peters; Thomas F. Schuessler, Hillsboro, both of Mo.

[73] Assignee: Sherwood Medical Industries Inc., St. Louis, Mo.

[21] Appl. No.: 225,577

[22] Filed: Jan. 16, 1981

[51] Int. Cl.³ .............................................. A61M 1/00
[52] U.S. Cl. ..................... 128/276; 128/247
[58] Field of Search ............... 285/200, 260; 215/309; 220/403, 404; 128/276, 275, DIG. 24, 247, 760; 55/524, 527

[56] References Cited

U.S. PATENT DOCUMENTS

| | | | |
|---|---|---|---|
| 3,699,815 | 10/1972 | Holbrook | 128/276 |
| 3,814,098 | 6/1974 | Deaton | 128/276 |
| 3,848,628 | 11/1974 | Deaton et al. | 128/276 |
| 3,866,608 | 2/1975 | Reynolds et al. | 128/276 |
| 4,111,204 | 9/1978 | Hessel | 128/276 |
| 4,235,229 | 11/1980 | Ranford | 128/207.17 |
| 4,275,732 | 6/1981 | Geveg | 128/276 |

*Primary Examiner*—Kyle L. Howell
*Assistant Examiner*—J. L. Kruter
*Attorney, Agent, or Firm*—Stanley N. Garber; William R. O'Meara

[57] ABSTRACT

A medical drainage collection device of the disposable liner type wherein the problems of connecting and disconnecting the liner from the canister of a device is simplified by providing a resilient locking device on a canister cover which receives a snap-in tube connector fixed to the disposable liner. Pressure applied to the locking device resiliently releases the connector from the cover. The liner can be provided with a hydrophobic filter which filters air before reaching the vacuum system to prevent system contamination, and when covered by drainage liquid closes off further gas or air flow through the filter to also provide a maximum-fill shut-off thereby preventing overfilling.

21 Claims, 5 Drawing Figures

BODY FLUID COLLECTION DEVICE WITH DISPOSABLE LINER

DESCRIPTION

1. Technical Field

This invention relates to body fluid drainage collection devices and more particularly to such devices that are connectable to a suction source and which have a disposable liner.

2. Background Art

As is well known, body fluid collection devices, such as reusable suction canisters of the disposable liner type, have been used to collect body fluids, for example, blood and other exudates from a wound, such as caused by surgery, in order to facilitate healing. While reusable canisters of the disposable liner type avoid the problems of emptying and cleaning a used canister, they are not free of problems. For example, in some cases removal of the bag requires opening the canister and then closing the bag, for example, with a string, or with some constructions, the upper lid of the canister, which lid can be relatively expensive, is discarded with the filled liner. In using some canisters, an external filter is required between the source of suction and the canister in order to ensure that the source of suction, such as a hospital source, is not contaminated by bacteria from the patient. Also, in some cases, it is necessary that an external, separate overfill limiting valve be used to prevent overfilling of the liner, and such valves increase the overall cost of the device.

DISCLOSURE OF THE INVENTION

The present invention is directed to overcoming one or more of the problems set forth above and has for its object to provide an improved drainage fluid collection device of the disposable liner type.

In accordance with the one aspect of the present invention, a body drainage collection device is provided which has a canister with a removable lid and a flexible liner removably insertable into the canister. The liner has a connector removably insertable into an opening in the canister for connection with a body cavity. The liner has a gas passage which effects fluid communication between the interior of the liner and the interior of the canister when the liner is in the canister. The canister has another opening for connecting the interior of the canister with a source of suction. In accordance with another aspect of the invention, a hydrophobic filter is disposed on a canister liner to provide gas communication between the interior of a liner and the interior of a canister containing the liner.

These as well as other objects and advantages of the present invention will become apparent from the following description and accompanying drawings.

DESCRIPTION OF THE PREFERRED EMBODIMENT

Figure 1:
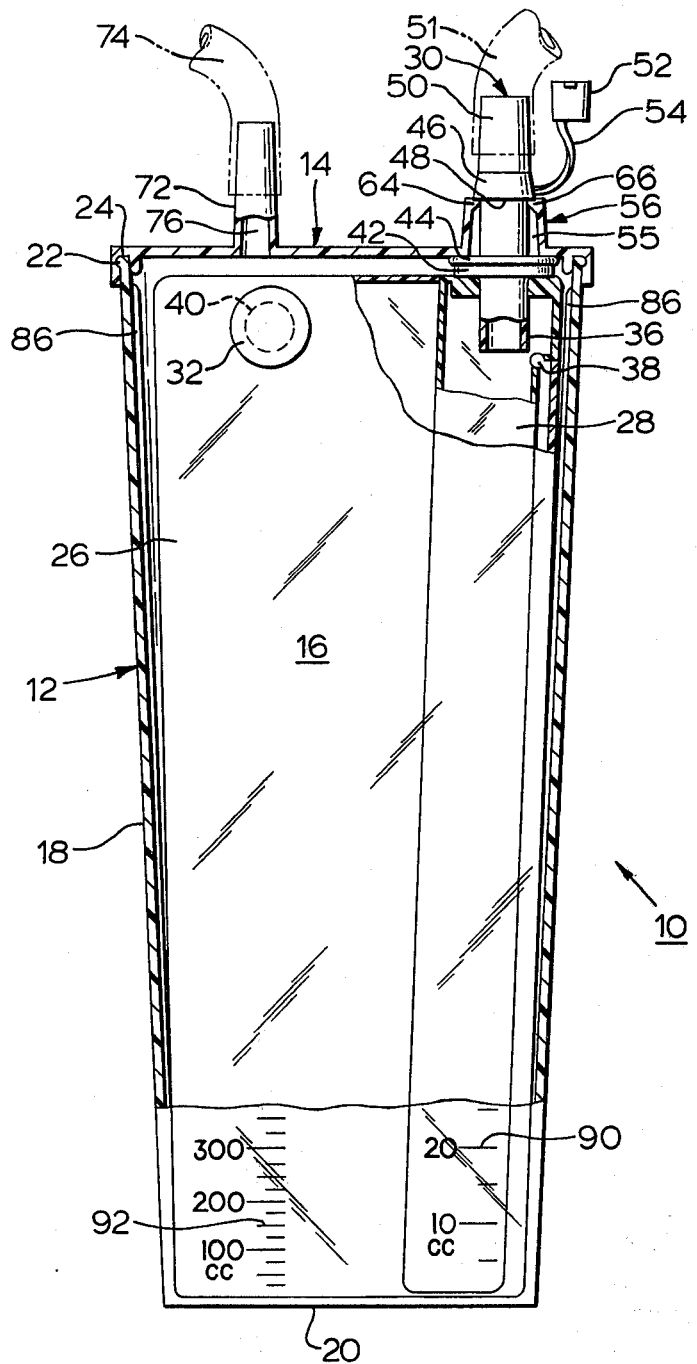
FIG. 1 is an elevational view, partly in cross-section and with some parts broken away, of a drainage collection device in accordance with the present invention.

Referring now to the drawings and particularly to FIG. 1, a body drainage or fluid collection device 10 is shown including a canister 12 having a canister cover or lid 14, and a bag or liner assembly 16 disposed of within the canister 12.

The canister 12 includes a generally cylindrical or slightly conical canister body or container 18 closed at the lower end by a bottom wall 20 integral with the container. The container 18 has an upper open end with a radially outwardly extending peripheral bead 22 at the upper end. When the cover 14 is placed onto the upper end of the container 18, the bead 22 snaps into a peripheral groove 24 provided in the bottom side of the cover 14 to effect a peripheral fluid tight seal between the cover 14 and container 18.

The container 18 is preferably made of a relatively rigid or hard plastic, for example, transparent polystyrene or the like. The cover 14 is preferably made of a semi-rigid plastic, for example, a medium density polyethylene. The cap 14 should be flexible enough to be snapped onto the upper end of the rigid container as previously mentioned, and such that it can be removed from the canister without permanent deformation. In other words the cap 14 should be sufficiently rigid but flexible enough to be attached and detached from the canister 12 repeatedly. Other well known materials such as plastic materials other than the above mentioned ones may, of course, be used to form or mold the cover 14 and container 18 where desired.

The liner assembly 16 is shown in FIG. 1 disposed in the canister 12 in its expanded condition. The liner assembly includes a pliable, outer main drainage collection container or bag 26 and a pliable inner smaller or pediatric collection container or bag 28 within bag 26. The liner assembly 16 also includes a connector such as a tubular tube connector 30 extending through the assembly and into the pediatric bag 28, and a filter and valve member 32 which provides a gas flow passage between the interior of bag 26 and the interior of the canister 12 exteriorly of the bag 26, as will be discussed hereafter.

Figure 2:
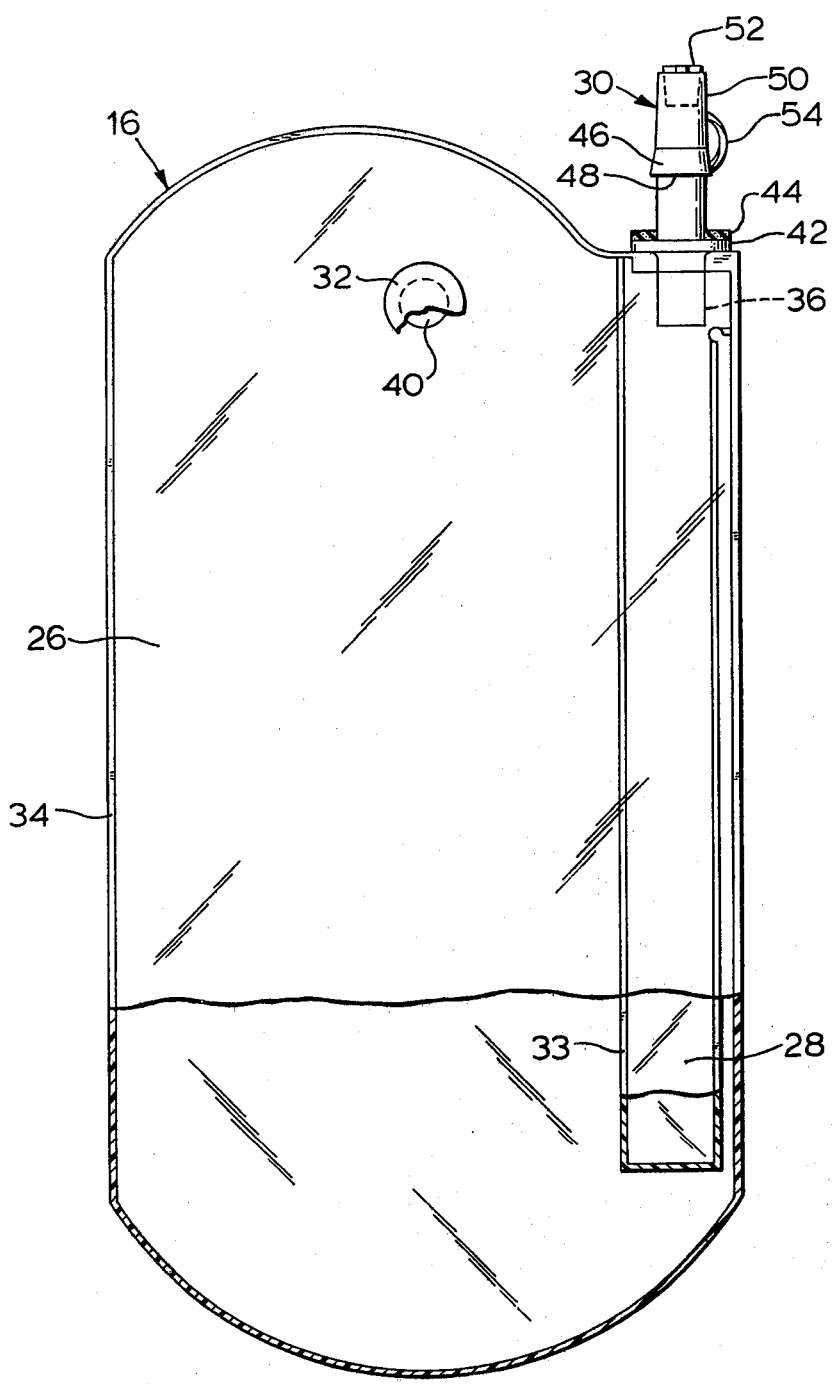
FIG. 2 is an elevational view of the liner assembly of FIG. 1.

The liner assembly 16 is shown in a flattened or uninflated condition in FIG. 2. Assembly 16 may be made, for example, by employing a conventional cutting and radio frequency (RF) sealing die to produce seal lines in plastic sheet material and form the inner and outer bags 26 and 28. For example, a pair of plastic sheets such as of pliable polyvinyl chloride, may be RF sealed together along a seal line indicated at 33 to form the inner bag 28, the upper end being temporarily left unsealed. Similarly, two sheets of plastic such as polyvinyl chloride, may be RF sealed along a seal line 34 to form the outer collection bag 26, the bag being temporarily left unsealed in the upper right hand corner as viewed in FIGS. 1 and 2. The inner bag may be placed into the outer bag with the unsealed upper facing margins of the inner bag 28 between the unsealed upper right hand corner margins of the outer bag 26. The tubular connector 30 is positioned with its lower end portion 36 received in the upper end of the inner bag 28. With the connector so located, the bags are sealed to each other and to the connector portion 36 to completely seal the perpheries of the bag closed about the connector. This may be performed by RF sealing or any other suitable sealing process. The inner bag 28 is provided with an opening 38 located offset from the longitudinal axis of connector 30 and near the upper end of the bag. Thus, the bags 26 and 28 are completely sealed except that they are connected in fluid communication with connector 30, which extends into bag 28, and the interior of canister 12 outside the bag assembly 16 by means of the filter 32.

Filter 32 is a hydrophobic filter made of a filter material covering an opening 40 in the upper portion of bag 26 and which passes gas such as air from the interior of the bag assembly 16 when not covered by a liquid. Filter 32 also prevents or inhibits bacteria from passing through it, and prevents gas and liquid from flowing through it when the inner surface of the filter is covered by liquid, such as water or body drainage liquid. In this way, bacteria is inhibited from entering the suction system, such as a hospital vacuum system. Also, since the filter 32 is hydrophobic it acts as a maximum-fill valve preventing overfilling, that is, when the liquid drainage covers the inner side of filter 32, gas ceases to flow through the filter stopping further drainage collection.

The filter 32 is preferably made of a material known under the trademark "Tyvek" produced by E. I. duPont de Nemours and Company, Inc. of Wilmington, Delaware. "Tyvek" sheet is a spunbonded olefin and is a network of minute polyethylene fibers approximately 1/5000 inch in diameter. The sheet web of "Tyvek" is made by an integrated spinning and bonding process in which a random distribution of continuous polyethylene fibers are self-bonded (no binders are used) by heat and pressure. Good results were obtained using "Tyvek" No. 1073B. Other suitable hydrophobic filters are usable. For example, an "Acropor" filter made of acrylonitrile polyvinyl chloride reinforced with nylon may be used in some cases. The "Acropor" filter may be obtained from Gelman Instrument Company, 600 South Wagner Road, Ann Arbor, Mich.

The tube connector 30 has an integral peripheral flange 42 which receives a resilient annular seal 44 such as of rubber or soft plastic. The connector 30 extends upwardly and has a downwardly and outwardly flaring skirt 46 providing a flat, annular bottom wall or flange 48 spaced from the annular flange 42. The connector extends upwardly and has an upper end, tapered tube connector portion 50 adapted to sealingly receive a tube or catheter, such as indicated at 51 in FIG. 1 that is adapted to be inserted into a body cavity or the like that is to be drained of fluid. The connector 30 also has a stopper 52 connected to the connector by a strap 54, the strap 54 being long enough to permit insertion of the stopper 52 into the upper end of the connector 30 such as shown in FIG. 2. The connector 30 including the stopper 52 and strap 54 may be formed as an integral molded part, for example, of a suitable moderately rigid polyvinyl chloride plastic material.

With the connector stopper 52 disposed in the connector 30, the connector can be inserted through a passage 55 in a releasable locking member 56 to secure it to the canister 12. The locking member 56 is shown on the cover 14 to connect the liner assembly 16 directly to the cover. Assembly 16 such as when in the uninflated condition of FIG. 2 is connected to cover 14 and then is inserted into canister 18, and the attached cover 14 snapped into sealing engagement with the upper end of the container as in FIG. 1.

Figure 3:
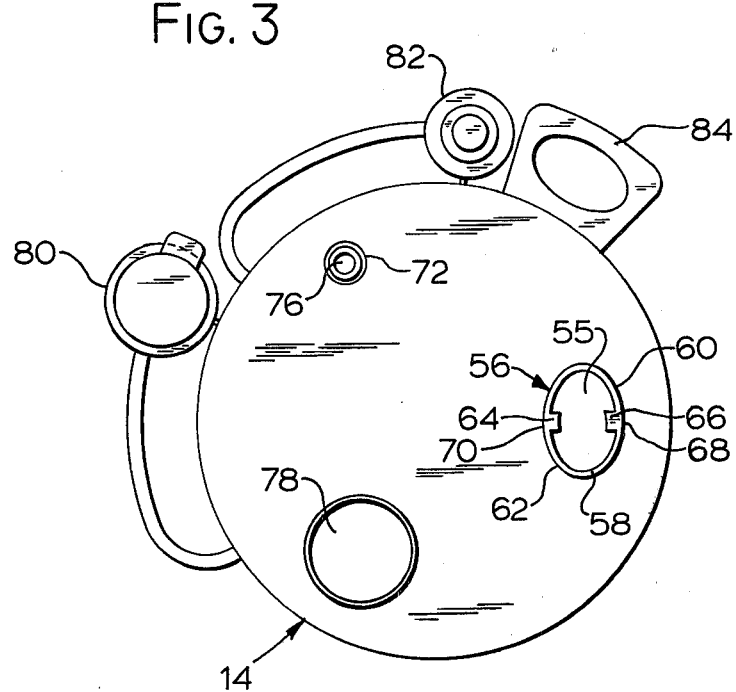
FIG. 3 is a top plan view of the lid of the collection device of FIG. 1.
Figures 4, 5:
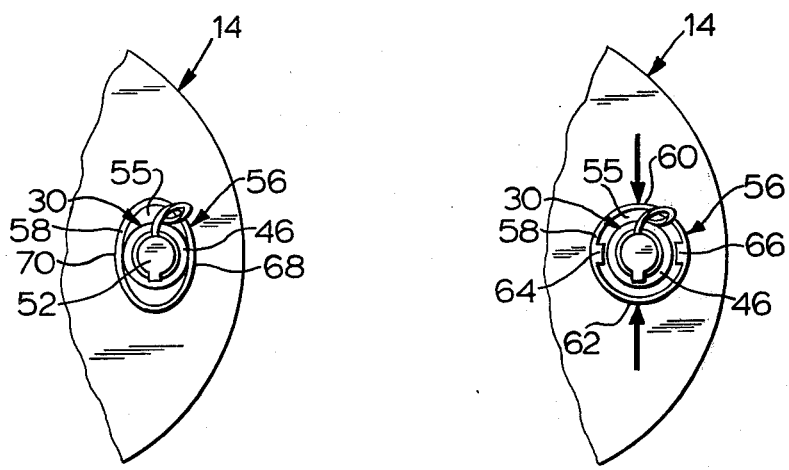
FIG. 4 is a fragmentary top plan view of the lid of FIG. 3 with the liner assembly of FIG. 1 disposed in place for operation.
FIG. 5 is a fragmentary top plan view illustrating forces applied to portions of the lid to effect release of the liner assembly of FIG. 1 from the lid.

The locking member 56 is shown as an integral portion of cover 14 and, as also seen in FIGS. 3 and 4, has an upwardly extending flexible, noncircular wall 58. Wall 58 has a generally eliptical configuration in cross-section and as viewed in FIGS. 3 and 4. It has opposed ends 60 and 62 on the longer axis of the eliptical configuration and a pair of integral locking surfaces or latch tabs 64 and 66 extending inwardly from the opposed sides 68 and 70 of the eliptical configuration along the shorter axis.

The connector 30 is dimensioned so that when inserted into the passage 55 in the cover locking member 56, the opposed sidewalls 68 and 70 and/or tabs 64 and 66 are resiliently forced outwardly or away from each other as the skirt 46 slides through the opening and between the tabs. When the skirt 46 passes the tabs 64 and 66, the tabs snap back and under the flange 48, the condition illustrated in FIGS. 1 and 4. In order to lock the connector to the cover 14 in this way, the gasket 44 is compressed against the underside of the cover about the bottom end of opening 55 so that the connector is tightly attached in place to the cover 14 with the gasket 44 sealingly closing the lower end of passage 55 about the connector. In other words, air in passage 55 of the locking member can not flow into the canister 12.

Cover 14 is also provided with a tubular integral tube connector 72 adapted for connection with a suction tube such as a tube 74 shown in fathom in FIG. 1. Tube connector 72 is adapted to be connected to a source of suction such as a conventional hospital suction system. Connector 72 has a passage 76 which communicates with the interior of the canister 12 exteriorly of the liner assembly 16. Cover 14 also includes a relatively large discharge or emptying port 78 which may be used to empty the canister where a liner assembly 16 is not utilized with the canister. When the liner assembly 16 is employed, a sealing cap 80 is placed onto the canister emptying port 78 to sealingly close it. Also a closure 82 can be used to close the vacuum tube connector 76 when it is desired to transport a filled canister (without a liner assembly 16) to a location where the canister is to be emptied. There is also a handle 84 extending outwardly from one side of the cover 14 which can be grasped to facilitate connecting the cover 14 to the canister and for removing the cover from the canister. All parts of cap 14 are integrally formed.

The upper and lower ends of outer collection bag 26 curves outwardly when the bag is flattened or evacuated such as shown in FIG. 2 but the bag 26 substantially completely fills the canister 12 when operating suction is applied to the canister causing the bags 26 and 28 to expand as in FIG. 1. The upper and lower ends tend to become flattened as the bag is inflated. In order to prevent the air from being trapped in the lower portions of the canister and the liner assembly 16 from expanding fully to the lower end of the canister, a plurality of vertical ribs 86 (FIG. 1) are formed on the inner wall of container 18. For example, four ribs 86 circumferentially spaced apart may be used (only two ribs 86 are in view in FIG. 1). In this way, the bag is spaced from the sidewalls at the ribs since the bag cannot completely conform to the ribs or seal around the ribs. Thus, the ribs and bag form vertical channels from the bottom wall 20 upwardly to the upper end portion of the canister so that air can flow along these channels formed between the bag and the sidewalls of the ribs. If desired, instead of ribs 86, grooves (not shown) can be formed in the sidewall of the container 18 to effect air channels from the bottom to the top of the container to serve the same purpose as ribs 86.

In use, when the tube connector 72 is connected to a vacuum source, air will flow in connector 30, into the inner bag 28, through the opening 38, into the outer bag 26, through opening 40 and the hydrophobic filter 32 into the interior of canister 12 exteriorily of liner or bag assembly 16, into the passage 76 of vacuum connector 72 and then into the vacuum system by means of tube 74. Because of this flow the bags inflate and substantially fill the interior of canister 12. The bags inflate since there is a pressure differential across the filter since it provides a resistance to air flow through it. The inner and outer container bags remain inflated as suction is applied. When the catheter is inserted into the cavity or wound to drain fluid drainage from the patient, the drainage fluid flows into the connector 30 and directly into the smaller inner bag 28 to fill it. If the small inner bag 28 fills with drainage liquid which reaches the outlet 38, the drainage fluid flows through outlet 38 and into the interior of the main collection bag 26 to start filling bag 26. The inner bag 28 can serve as a pediatric collection bag. The canister is provided with graduations or calibrations indicated at 90 in cubic centimeters to show the volume of collection material filling the inner bag 28 at any given time. Calibrations 92 indicate the volume of drainage fluid in the larger bag 26 at any given time during collection. These calibrations extend up to an upper portion of the assembly 16.

When it is desired to disconnect the collection device 10 from the vacuum source and the patient, the tube 74 and catheter 51 are removed from the connector 72 and connector 30, respectively. The stopper 52 is then inserted into the upper end of connector 30 to sealingly close off the outer end of the connector. Next, the cover 14 maybe grasped, by the handle 84 (FIG. 3) and snapped off the upper end of the canister container 18. By raising the cover 14, the filled liner assembly 16, since it is connected to it, moves upwardly and out of the canister. The cover 14 and assembly 16 can then be transported to a location adjacent a disposal system.

The connector 30 with the liner assembly 16 attached is removed from the cover 14 by applying clamping forces, as indicated by arrows in FIG. 5, to the opposite ends 60 and 62 of the locking member 56 to cause the oblong or eliptical wall 58 to become substantially circular as shown in FIG. 5. It will be seen that the locking surfaces or tabs 64 and 66 move away from each other and outwardly from the flange 48 on the bottom of skirt 46 to thereby allow the skirt and connector to move downwardly through the opening 55 thereby removing the cover from the connector 30. The closed and filled liner assembly 16 may then be discarded and the cover 14 retained for further use with a new liner assembly.

By employing a hydrophic, bacterial filtering filter such as filter 32 on the upper portion of the outer bag 26, the necessity for an external bacterial filter and an external maximum-fill valve is avoided.

The filter 32 also provides a restricted air flow path between the interior of the outer bag 28 and the interior of the canister to allow expansion of the bag 28 during suctioning. The amount of air flow can be adjusted by varying the size of hole 40 in the bag 26 and the effective surface area of the filter.

The bag assembly 16 is easily connected to and released from the cover 14, which cover is reusable with other bag assemblies. Since the stopper 52 of the bag may be inserted into connector 30 to seal the bag assembly 16 before removal of the assembly from the cover 14, there is substantially less chance of the content of the bag assembly contaminating the person handling the drainage device.

As various changes could be made in the above construction without departing from the scope of the invention, it is intended that all matter contained in the above description and shown in the accompanying drawings shall be interpreted as illustrative and not in a limiting sense.

We claim:

1. A body drainage collection device comprising a canister having interior and exterior sides and including a container closed at the lower end and open at the upper end and a removable cover for sealingly closing the upper end of said container, and a disposable liner removably insertable into said container and including a pliable bag having upper and lower end portions, fluid connector means sealingly connected to the upper end portion of said bag in fluid communication with the interior of said bag and having an outer portion externally of said bag for connection with the body of a patient, and gas passage means adjacent the upper end portion of said bag for allowing gas to flow from the interior to the exterior of said bag, said canister having releasable locking means for said connector means on an upper portion thereof including an opening through said canister upper portion for receiving said outer portion of said connector means and releasably locking said connector means to said canister, and lock release means on and manually operable from the exterior side of said canister upper portion for releasing said locking means to release said connector means and bag from said canister, and means for connecting the interior of said container to a source of suction.

2. The device of claim 1 or wherein said releasable locking means is on said cover.

3. The device of claim 1 wherein said connector means comprises a generally tubular member and said outer portion thereof is adapted to frictionally receive a tube for connection to the body of a patient.

4. A body drainage collection device comprising a canister including a container closed at the lower end and open at the upper end, and a removable cover for sealingly closing the upper end of said container, and a disposable liner removably insertable into said container and including a pliable bag having upper and lower end portions, fluid connector means sealingly connected to the upper end portion of said bag in fluid communication with the interior of said bag and including a generally tubular member having an outer portion externally of said bag for receiving a tube for connection with the body of a patient, and gas passage means adjacent the upper end portion of said bag for allowing gas to flow from the interior to the exterior of said bag, said canister having releasable locking means on said cover for said connector means on an upper portion thereof including an opening through said canister for receiving said outer portion of said connector means and releasably locking said connector means to said canister, and manually operable means at the exterior of said canister for releasing said locking means to release said connector means from said canister, and means for connecting the interior of said canister to a source of suction, said connector means having flange means thereon, said locking means including latch means movable to a locking position between said flange means and said container to secure said connector means to said canister.

5. The device of claim 4 wherein said latch means are normally resiliently urged toward the locking position and manually movable to a release position to allow removal of said connector means from said locking member.

6. The device of claim 5 further including a gasket surrounding said connector means and compressed between said flange and an interior surface of said canister when said connector means is in said locking position to effect a fluid tight seal closing said opening about said connector means.

7. The device of claim 4 wherein said releasable locking means includes flexible, resilient walls extending outward from said canister defining said opening, said latch means being on said walls.

8. The device of claim 7 wherein said resilient walls are integral with said cover and are normally generally oblong in configuration, said latch means being integral portions of said walls and including opposed surfaces of said walls spaced across the shorter axis of the oblong configuration, said flange means on said connector means having a dimension greater than the space between said opposed surfaces when said connector means is in the locked condition, said manually operable means including opposed surfaces of said walls spaced along the longer axis of said configuration and movable toward each other in response to clamping forces applied thereto to cause the space between said opposed surfaces to increase and release said connector means from said canister.

9. A body drainage collection device comprising a canister including a container closed at the lower end and open at the upper end, and a removable cover for sealingly closing the upper end of said container, and a disposable liner removably insertable into said container and including a pliable bag having upper and lower end portions, fluid connector means sealingly connected to the upper end portion of said bag in fluid communication with the interior of said bag and having an outer portion externally of said bag for connection with the body of a patient, and gas passage means adjacent the upper end portion of said bag for allowing gas to flow from the interior to the exterior of said bag, said canister having releasable locking means for said connector means on an upper portion thereof including an opening through said canister for receiving said outer portion of said connector means and releasably locking said connector means to said canister, and manually operable means at the exterior of said canister for releasing said locking means to release said connector means from said canister, a second bag smaller than said first named bag disposed within said first named bag and connected to said connector means to receive the initial flow of drainage fluid into said canister, said second bag having an opening in the upper portion thereof connecting with the interior of said first named bag whereby drainage is capable of overflowing into said first named bag through said bag opening during use of the device, and means for connecting the interior of said container to a source of suction.

10. The device of claim 9 wherein said container and said bags are of transparent, and said canister includes indicia means thereon for determining the quantity of drainage respectively in said first and second named bags.

11. A body drainage collection device comprising a canister including a container closed at the lower end and open at the upper end, and a removable cover for sealingly closing the upper end of said container, and a disposable liner removably insertable into said container and including a pliable bag having upper and lower end portions, fluid connector means sealingly connected to the upper end portion of said bag in fluid communication with the interior of said bag and having an outer portion externally of said bag for connection with the body of a patient, and gas passage means adjacent the upper end portion of said bag for allowing gas to flow from the interior to the exterior of said bag, said canister having releasable locking means for said connector means on an upper portion thereof including an opening through said canister for receiving said outer portion of said connector means and releasably locking said connector means to said canister, and manually operable means at the exterior of said canister for releasing said locking means to release said connector means from said canister, said container including means forming channels between said bag and the inner wall of said container that extend between a bottom portion of said container and an upper position thereof when said bag is expanded during use of said device, and means for connecting the interior of said container to a source of suction.

12. A body drainage collection device comprising a canister including a container closed at the lower end and open at the upper end, and a removable cover for sealingly closing the upper end of said container, and a disposable liner assembly removably insertable into said container including a first pliable plastic bag, a second pliable plastic bag smaller than and disposed in said first bag, each of said bags having upper and lower end portions, said second bag being connected at the upper end portion to the upper end portion of said first bag and having an opening adjacent the upper end thereof communicating the interior of said second bag with the interior of said first bag, filter means in the upper end portion of said first bag effecting gas communication between the interior of said first bag and the interior of said canister exteriorly of said first bag, a tube connector sealingly connected to said liner assembly in direct fluid communication with the interior of said second bag, said connector having a distal end portion extending out of said liner assembly and having flange means thereon, said cover having a tubular coupling extending therefrom adapted for connection with a source of suction for connecting the interior of said canister with said source of suction, said cover including releasable locking means having upwardly extending resilient walls defining a passage through said cover and latching surfaces on said walls, said connector means being insertable into said passage means to effect movement of said flange means past said latching surfaces to effect movement of said latching surfaces under said flange means to lock said connector means to said cover, said walls being resiliently manually movable to effect unlatching movement of said latching surfaces to release said connector means from said cover.

13. The device of claim 12 wherein said connector means has gasket means surrounding said connector means and closing said cover passage when said connecting means is locked to said cover.

14. The device of claim 12 wherein said filter is a hydrophobic filter.

15. The device of claim 14 wherein said container includes means spacing portions of said first bag from the inner sidewalls when the device is in use to provide gas channels extending from the lower portion of the interior of said container to thereby remove air therefrom when a suction source is connected to said tubular coupling.

16. The device of claim 15 wherein said spacing means includes a plurality of ribs spaced around said container and extending between the bottom of said container to a point adjacent the upper end thereof.

17. The device of claim 14 wherein said connector means includes a resilient stopper connected thereto and movable through said passage when said connector means is inserted in said passage means.

18. The device of claim 12 wherein said walls of said locking means normally having a generally eliptical configuration, said latching surfaces include a surface on each of opposed sides of said passage along the short dimensions of the eliptical configuration, said walls becoming generally circular in shape in response to clamping pressures applied to said walls on the opposed sides of said passage along the longer dimension of the eliptical configuration to allow release of said connector means from said cover.

19. A body drainage collection device comprising a canister including a container closed at the lower end and open at the upper end, and a removable cover for sealingly closing the upper end of said container, and a disposable liner removably insertable into said container including a pliable bag having upper and lower end portions, and fluid connector means sealingly connected to the upper end portion of said bag in fluid communication with the interior of said bag, means for removably connecting said connector means to said canister with the connector means extending through said canister for connection with the body of a patient, filter means on the upper portion of said bag effecting gas communication between the interior of said bag and the interior of said container exteriorly of said bag, means for connecting the interior of said container to a source of suction so that gas flows from said connector means into said bag and through said filter to the interior of said canister when the device is in use, said filter being a hydrophobic material which when covered by liquid drainage prevents fluid flow therethrough, and a second bag smaller than said first named bag disposed within said first named bag and connected to said connector means to receive the initial flow of drainage fluid into said canister, said second bag having an opening in the upper portion thereof connecting with the interior of said first named bag whereby drainage is capable of overflowing into said first named bag through said opening during use of the device.

20. A body drainage collection device comprising a canister including a container closed at the lower end and open at the upper end, and a removable cover for sealingly closing the upper end of said container, and a disposable liner removably insertable into said container including a pliable bag having upper and lower end portions, and fluid connector means sealingly connected to an upper end portion of said bag in fluid communication with the interior of said bag, means for removably connecting said connector means to said canister with the connector means extending through said canister for connection with the body of a patient, filter means on the upper portion of said bag effecting gas communication between the interior of said bag and the interior of said container exteriorly of said bag, and means for connecting the interior of said container to a source of suction so that gas flows from said connector means into said bag and through said filter to the interior of said canister when the device is in use, said filter being a hydrophobic material which when covered by liquid drainage prevents fluid flow therethrough, said container including means forming channels between said bag and the inner wall of said container that extend between a bottom portion of said container and an upper position thereof when said bag is expanded during use of said device.

21. The device of claim 20 wherein said means for removably connecting said connector means is on said cover, and said means for connecting the interior of said container to a source of suction includes tubular connection means in said cover.

* * * * *